United States Patent [19]

Bedi et al.

[11] Patent Number: 4,724,839
[45] Date of Patent: Feb. 16, 1988

[54] SURGICAL FASTENING SYSTEMS MADE FROM POLYMERIC MATERIALS

[75] Inventors: James J. Bedi, Stockton; Anthony S. Miksza, Jr., Jersey City; Carl R. Smith, Bloomingdale, all of N.J.

[73] Assignee: Ethicon, Inc., Somerville, N.J.

[21] Appl. No.: 908,552

[22] Filed: Sep. 18, 1986

[51] Int. Cl.$^4$ ............................................. A61B 17/04
[52] U.S. Cl. .............................. 128/334 C; 128/334 R
[58] Field of Search ........................ 128/334 C, 334 R

[56] References Cited

U.S. PATENT DOCUMENTS

| | | | |
|---|---|---|---|
| 4,060,089 | 11/1977 | Noiles | 128/334 C |
| 4,402,445 | 9/1983 | Green | 128/334 C |
| 4,534,350 | 8/1985 | Golden et al. | 128/334 C |

Primary Examiner—Richard C. Pinkham
Assistant Examiner—Gary Jackson
Attorney, Agent, or Firm—Richard J. Grochala

[57] ABSTRACT

An improved surgical fastener system comprising staples and receivers with flanges on the staple legs interlocking with openings in the receiver.

Each staple is of polymeric material and U-shaped with a pair of parallel legs joined by a bridging member. Each leg is tapered from a large cross section at the bridging member to a pointed end. There are at least two spaced flanges on each leg with the area between those flanges being cut away. Each flange extends only part way around the circumference of a leg.

1 Claim, 7 Drawing Figures

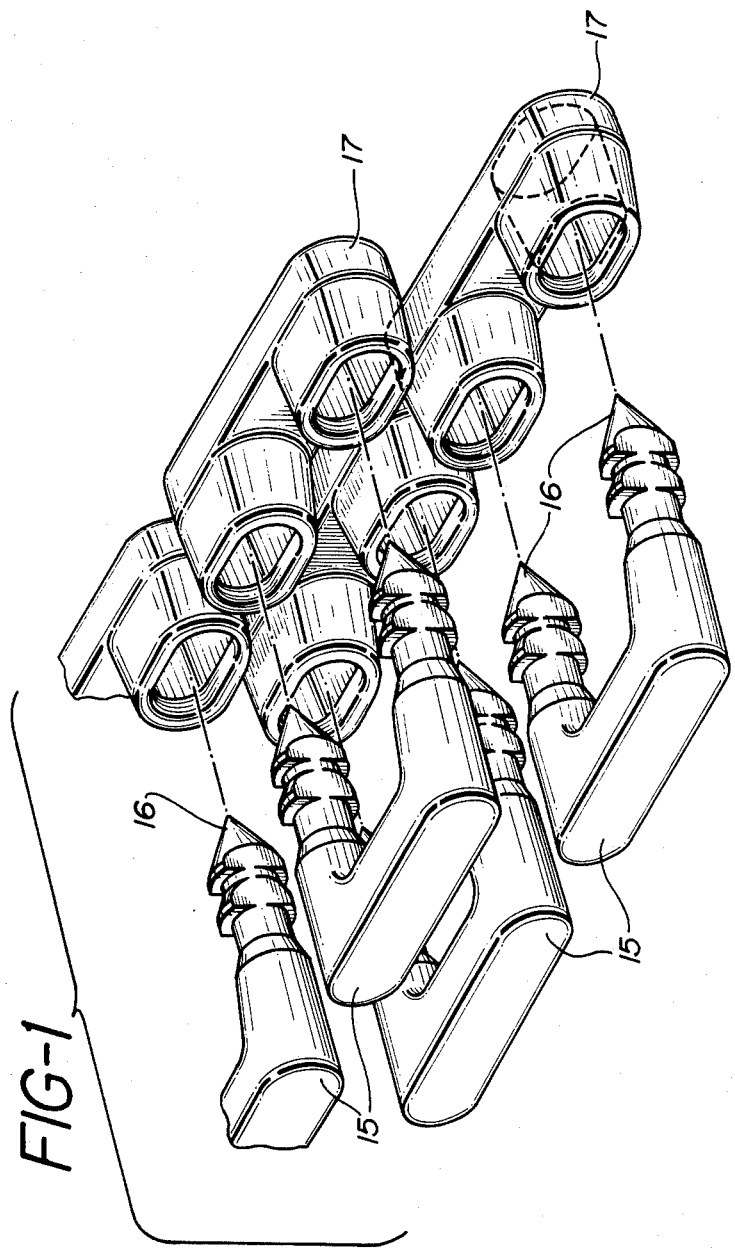

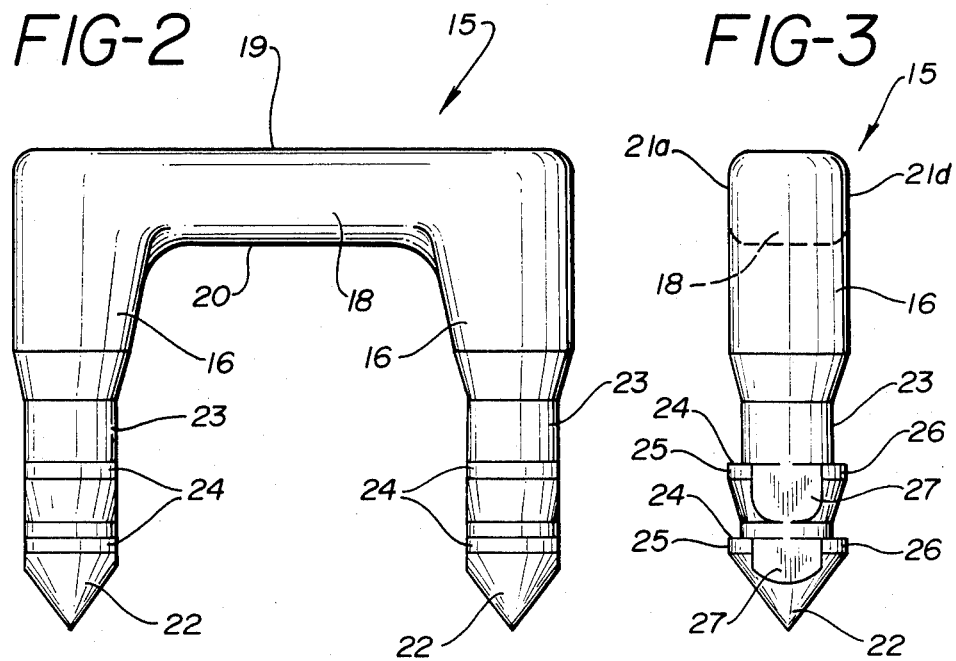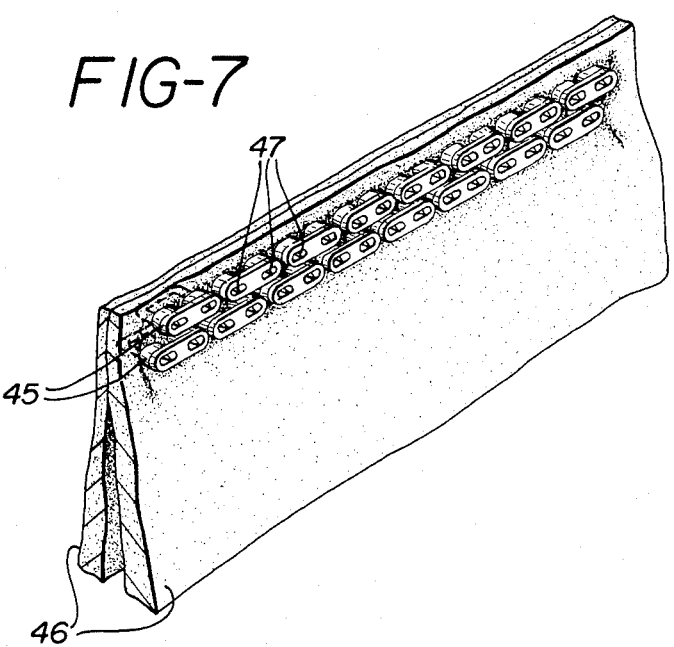

SURGICAL FASTENING SYSTEMS MADE FROM POLYMERIC MATERIALS

The present invention relates to surgical fastening systems for closing wounds and more particularly to surgical fastening systems made from polymeric materials for use in closing internal wounds in humans or animals.

BACKGROUND OF THE INVENTION

For many years surgical wounds and other internal and skin wounds, have been closed using sutures and needles. In more recent times a number of skin stapling instruments have been developed. These instruments apply a series of metal staples to an external wound; that is, a skin wound, to close the wound. In many instances, such skin stapling instruments have replaced the suturing of such wounds. Also, in more recent times instruments have been developed to apply metal fasteners such as staples internally to close internal wounds during a surgical procedure. The primary advantages of the instruments which apply staples to wounds is that they greatly reduce the time required to close the wound and present minimum traumatic effects to improved healing of tissue. Both factors lead to reduced blood loss and improved patient care. Thus, these instruments have considerable medical benefits and economic benefits in surgical procedures. A major disadvantage of closing wounds with metallic staples is that very often the patient requires subsequent diagnostic procedures such as x-rays, CT scanning, and the like, and the metal staples often disrupt such diagnostic procedures. To overcome this last drawback, a number of polymeric fastening systems have been developed which use fasteners made from polymeric materials placed by a suitable instrument to close the wound. Examples of such fastening systems are more fully disclosed in U.S. Pat. Nos. 4,060,089, 4,532,927, 4,532,926 and 4,513,746.

In European patent application No. 84401937.2, Publication No. 0136949, there is disclosed a surgical fastening system made from polymeric materials which has a primary use of closing internal wounds. The system comprises a two-piece fastening member that is a staple which penetrates the tissue to be closed and a retainer or receiver which interlocks with that staple once it has penetrataed the tissue to maintain the wound closed. In this patent, the retainers are connected to one another by yieldable links, that is, flexible or frangible links. The links are used to maintain the receivers together to assist in loading instruments with the receivers, and it is desired that once applied to the tissue the links break so as not to restrict movement of the tissue.

When making polymeric fastening systems of either absorbable or non-absorbable polymers, the staple legs should penetrate the tissue with the least amount of trauma. Once the legs have penetrated the tissue, they should be reliably locked in place by the receiver. To lessen tissue trauma, it is desirable to reduce the insertion force required for the staple leg to penetrate tissue. The insertion force may be reduced by reducing the cross-sectional area of the staple leg. However, the smaller the cross-sectional area of a staple leg, the more it is apt to deform or misalign with the opening in the interlocking receiver.

What has now been discovered is a specific structure of a fastening system comprising staples and receivers wherein the insertion force to insert a staple leg through tissue is reduced and the misalignment of the staple leg and the receiver opening is also reduced while maintaining a reliable interlocking of the staple and receiver.

SUMMARY OF THE PRESENT INVENTION

Instruments used in the internal fastening of wounds generally apply at least two parallel rows of staples. When applying fasteners of absorbable materials, the instrument will apply at least a pair of parallel rows of staples, and a pair of parallel rows of receivers. The staples each comprise a pair of legs connected at one end by a bridging member, with the free end of the legs of the staples being sharpened or otherwise adapted to penetrate the tissue. The staple is applied to the tissue by penetrating the tissue with the legs so that the bridging member lies adjacent the tissue. A receiver, generally a member which has a pair of apertures spaced so that the legs will fit therethrough, is placed on the opposite side of the tissue and the apertures or openings in the receiver engage with the legs of the staple to lock the staple and receiver together and join the tissue. Hence, the instrument described above is carrying at least two parallel rows of staples in one jaw of the instrument, and at least two parallel rows of receivers in the opposite jaw of the instrument. The tissue to be joined is placed between the jaws of the instrument, the jaws are brought together, and the staple or staples fired so that the legs penetrate the tissue and engage the openings in the receivers and then the staples and receivers are released from the instrument.

The improved fastening system of the present invention comprises a U-shaped staple, and a receiver which interlocks with the free ends of the staple legs. The legs of the staple are substantially parallel and are joined at one end of each leg by a bridging member. The bridging member has a top and bottom surface which are connected by side surfaces. The legs are disposed from the bottom surface of the bridging member at opposite ends of the bridging member. The free ends of the legs have a pointed configuration. The legs have a generally circular cross-section and are preferably tapered from a larger cross-sectional portion adjacent the bridging member to a smaller cross-section in the lower portion adjacent the free end of the leg. Each leg member has a locking means comprising a pair of flange portions extending outwardly from the surface of the lower portion of the leg. The flange portions extend from only the sides of the staple, and taper to the pointed free end. In the area between the flange portions the flange is cutaway to the surface of the lower portion of the leg. The receiver which engages the free ends of the staple legs has a generally longitudinally elongated configuration. At each end of the receiver is an oval opening with the longer dimension of the oval aligned in the longitudinal direction of the receiver. When the legs of the staple are pushed through the openings in the receiver they are pushed through to such a degree that the flange portion on the staple legs contacts the under surface of the receiver adjacent the openings.

BRIEF DESCRIPTION OF THE DRAWINGS

The invention will be more fully described in conjunction with the accompanying drawings wherein:

FIG. 1 is a perspective view of fastening systems of the present invention;

FIG. 2 is a front view of a staple member of the fastening system of the present invention;

FIG. 3 is an end view of the staple shown in FIG. 2;

FIG. 7 is a perspective view of the new fastening system joining tissue.

DETAILED DESCRIPTION OF THE DRAWINGS

Figure 4:
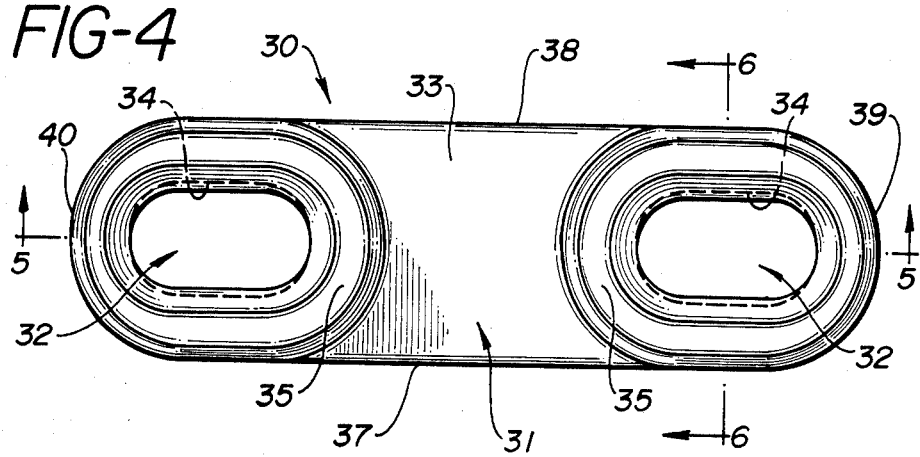
FIG. 4 is a top view of a receiver used in the fastening system of the present invention.

FIG. 1 shows parallel rows of fastening systems of the present invention in a perspective view. Each fastening system comprises a U-shaped staple 15 and a receiver 17. The legs 16 of the staples are designed to penetrate the tissue to be joined and lock or join therein to a receiver 17.

As more clearly shown in FIGS. 2 and 3, each staple 15 comprises a pair of legs 16. The legs are substantially parallel. The legs are joined at one end by a bridging member 18. The bridging member has a top surface 19, a bottom surface 20, and two side surfaces 21a and 21b connecting the top and bottom surfaces. Preferably the edges of the bridging member where the surfaces meet are smooth and rounded. The legs extend from the bottom surface at each end of the bridging member. In use, the legs penetrate the tissue to be joined, and the bridging member rests on the surface of one side of the tissue being joined. Each leg has a free end 22 which is pointed or sharapened to assist in penetrating the tissue. The legs have a generally circular cross-section and are preferably tapered from a larger cross-sectional portion adjacent the bridging member to a smaller cross-section in the lower portion 23, of the leg adjacent the free end of the leg. Disposed along the surface of the lower portion 23 of the legs are suitable means 24 for locking the legs of the staple with the receiver. In this embodiment, there are two locking means, 24 to adjust the distance between the staple and the receiver depending on the thickness of the tissue to be joined. As more clearly seen in FIG. 3, each locking means comprises a pair of flange portions, 25 and 26, extending outwardly from the surface of the lower portion of the leg generally orthogonally from a plane defined by the center lines of the lower portions of the two legs, and extending only partway around the circumference of the leg. The flange portions 25 and 26 of each pair, are aligned with respect to one another. The area 2 between the flange portions, is cut away to the surface of the lower portion of the leg to reduce the perimeter of the locking means and thereby reduce the force necessary to insert the staple legs and locking means through the tissue. The first pair of flange portions, closest to the pointed free end of each leg, taper to the pointed free end 22. The second pair of flange portions on each leg, disposed between the bridging member and the first pair of flange portions, and in alignment with said first pair, taper to the surface of the lower portion 23 of the leg.

Figure 5:
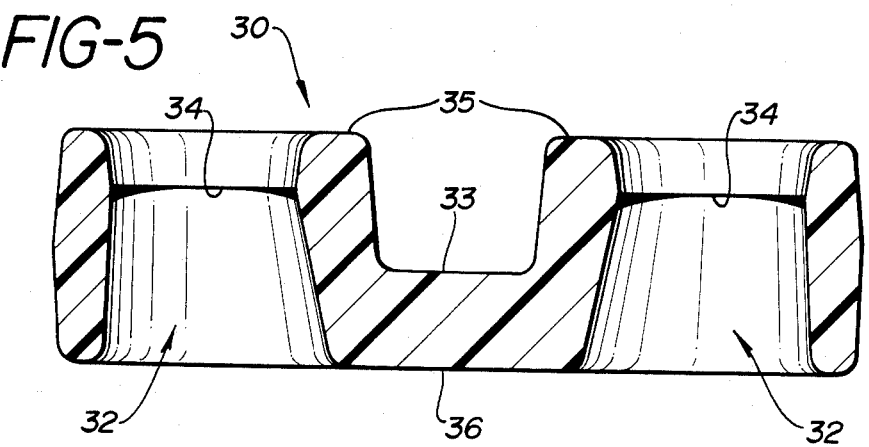
FIG. 5 is a cross-sectional view taken along line 5—5 of FIG. 4.
Figure 6:
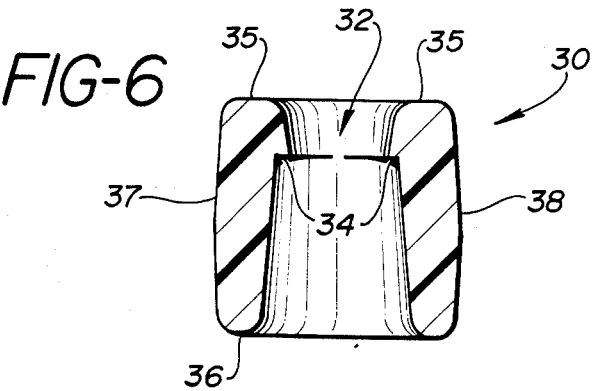
FIG. 6 is another cross-sectional view taken along line 6—6 of FIG. 4.

Individual receivers are more clearly depicted in FIGS. 4, 5 and 6. Each receiver 30 comprises a body member 31 having a generally longitudinally elongated shape. Disposed in that body member are two generally oval openings 32 with the longer dimension of said oval extending longitudinally of the receiver. The body member has a top surface 35, a bottom surface 36 and two side surfaces 37 and 38 connecting the top and bottom surfaces. The receiver also has rounded end surfaces 39 adn 40. As shown in FIG. 5, it is preferred that the center portion 33 of the body be depressed to allow the fastening system to be used with a broader range of tissue thickness. The center point of each opening preferably coincides or is spaced from the center point of the other opening by the distance between the center lines of the staple legs. By shaping the openings as shown, that is in an oval manner, the alignment of the staple legs and the openings is not as critical and if the staple legs tend to bend or get off line slightly when penetrating the tissue, they still will engage the oval openings of the receiver. In another preferred embodiment, the center point of each opening is spaced from the center point of the other opening by a distance slightly greater than the distance between the center lines of the staple legs, which decreases the firing force needed to insert the staple legs, through tissue and into the receiver. As shown in FIG. 6, immediately below the opening are inwardly extending flanges, 34. Once the staple leg penetrates the tissue the appropriate flange portion on the staple legs will be engaged by the flange in the opening to lock the staple leg therewith. If sufficient firing force is used, when thick tissue is being joined, the flange portions closest to the free end of the staple will engage the flange in the opening; whereas, if thinner tissue is being joined, the second pair of flange portions will engage the flange in the opening of the receiver. In the alternative, the surgeon may adjust the firing force such that the flange portions closest to the free end will engage the receiver flange, even if thin tissue is being joined.

FIG. 7 shows parallel rows of receivers 45 in place on one side of the tissue 46 being joined. The legs 47 of the staples on the opposite side of the tissue are locked in the openings of the receivers to hold the tissue together.

The fastening systems of the present invention may be made from any of the non-absorbable or absorbable polymeric materials. Examples of suitable polymers are the polyesters, polyamides, polyolefins, polymers and copolymers of lactide, glycolide, dioxanone, and the like.

Having now described the invention, it will be readily apparent to those skilled in the art that there are many variations and modfications which may be made to the invention without departing from the spirit and scope thereof.

What is claimed is:

1. A polymeric surgical fastening system for closing wounds, said fastening system comprising a U-shaped staple, and a receiver for adjustably interlocking with said staple;

said staple comprising, (a) a pair of substantially parallel legs, said legs being joined at one end thereof by a bridging member, the opposite end of each leg being a pointed free end having a generally circular cross-section and adapted to penetrate tissue, said bridging member having a top surface, a bottom surface, and a pair of side surfaces connecting said top and bottom surfaces, wherein the edges of the bridging member where the surfaces meet are smooth and rounded, said legs being disposed from said bottom surface, each leg having a lower portion, adjacent said free end, with a generally circular cross section, wherein the portion of each leg adjacent the bridging member has a circular cross-section larger than the circular cross section of the lower portion of said leg adjacent the free end and each leg of the staple is tapered from the larger cross-section portion to the smaller cross-section lower portion; and (b) adjustable locking means for adjusting the distance between the staple and receiver, the locking means comprising a pair of aligned flange portions extending outwardly from the surface of the lower portion of each leg, generally orthogonally from a plane defined by the longitudinal center lines of the lower portions of the two legs, and extending only part way around the circumference of the leg, the area between the flange portions being cut away to the surface of the lower portion of each leg on the inner and outer sides of the leg so that the flange portions only extend from two sides of the leg thereby reducing the cross-sectional area of the locking means, wherein a lower flange portion tapers to the pointed free end and an upper flange portion is disposed between the bridging member and the first flange portion; and said receiver adapted to engage the free ends of said leg members, said receiver having a generally longitudinally elongated configuration, a depressed top surface, bottom surface, a pair of longitudinally extending side surfaces connecting said top and bottom surfaces, and a pair of rounded end surfaces connecting said top and bottom surfaces and said side surfaces, and said receiver having a pair of openings extending from the top surface to the bottom surface, wherein the opening near the top surface is substantially the same size as the opening near the bottom surface, one of said openings being disposed adjacent one end surface of the reciever and the other of said openings being adjacent the other end surface of said receiver, said openings having a generally oval configuration with the larger dimension of said oval extending longitudinally of said receiver, wherein the center point of each opening of the receiver is spaced from the center point of the other opening by the distance between the longitudinal center lines of the staple legs and wherein there is an inwardly extending flange disposed in each opening of the receiver which is capable of engaging either the upper or lower flange portion of each staple leg, whereby when the legs of the staple are inserted into the openings of the receiver, the flange portions of the staple legs engage the openings of the receiver to lock the staple and receiver together in one of two different positions.

* * * * *